United States Patent
Tracey et al.

(10) Patent No.: US 9,981,979 B2
(45) Date of Patent: May 29, 2018

(54) PROCESS FOR THE FORMATION OF HYDROCODONE BITATRATE

(71) Applicant: Cambrex Charles City, Inc., Charles City, IA (US)

(72) Inventors: Michael Robert Tracey, Charles City, IA (US); Zhiming Eric Dong, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 0 days. days.

(21) Appl. No.: 15/523,054

(22) PCT Filed: Nov. 2, 2015

(86) PCT No.: PCT/GB2015/053288
§ 371 (c)(1),
(2) Date: Apr. 28, 2017

(87) PCT Pub. No.: WO2016/067054
PCT Pub. Date: May 6, 2016

(65) Prior Publication Data
US 2017/0327511 A1    Nov. 16, 2017

(30) Foreign Application Priority Data
Oct. 31, 2014 (GB) .................... 1419454.2

(51) Int. Cl.
| *C07D 489/04* | (2006.01) |
| *A61K 31/485* | (2006.01) |
| *C07D 489/00* | (2006.01) |
| *A61K 31/00* | (2006.01) |

(52) U.S. Cl.
CPC .......... *C07D 489/04* (2013.01); *A61K 31/485* (2013.01); *A61K 31/00* (2013.01); *C07D 489/00* (2013.01)

(58) Field of Classification Search
CPC ........................... C07D 489/04; A61K 31/485
USPC ........................................... 546/45; 514/282
See application file for complete search history.

(56) References Cited

U.S. PATENT DOCUMENTS

| 6,245,357 B1* | 6/2001 | Edgren ............... A61K 9/0004 424/468 |
| 9,273,060 B2* | 3/2016 | Matharu ............. C07D 489/02 |
| 2007/0072889 A1 | 3/2007 | Hagen et al. |
| 2009/0264454 A1 | 10/2009 | Nickell |
| 2013/0035488 A1 | 2/2013 | Jones et al. |

FOREIGN PATENT DOCUMENTS

| WO | 9944591 A1 | 9/1999 |
| WO | 2005100361 A1 | 10/2005 |
| WO | 2006099351 A2 | 9/2006 |

OTHER PUBLICATIONS

United Kingdom Search Report for Application No. GB1419454.2, dated Jul. 31, 2015.
Test No. 109: Density of Liquids and Solids, OECD Guidelines for the Testing of Chemicals Section 1: Physical-Chemical Properties, Oct. 2, 2012, OECD Publishing, Paris.
International Search Report from PCT/GB2015/053288, dated Feb. 8, 2016.

* cited by examiner

*Primary Examiner* — Charanjit Aulakh
(74) *Attorney, Agent, or Firm* — Lerner, David, Littenberg, Krumholz & Mentlik, LLP

(57) ABSTRACT

There is provided a novel process for the preparation of a hydrocodone salt. In particular, there is provided a novel process for the preparation of a free-flowing slurry of a hydrocodone salt, for example, a free-flowing slurry of hydrocodone bitartrate hemipentahydrate.

18 Claims, 2 Drawing Sheets

PROCESS FOR THE FORMATION OF HYDROCODONE BITATRATE

CROSS-REFERENCE TO RELATED APPLICATIONS

The present application is a national phase entry under 35 U.S.C. § 371 of International Application No. PCT/GB2015/053288 filed Nov. 2, 2015, which claims priority from GB 1419454.2 filed Oct. 31, 2014, all of which are incorporated herein by reference.

The present invention relates to a novel and efficient process for the formation of hydrocodone salts and pharmaceutical compositions thereof. In particular, it relates to a process for the formation of hydrocodone bitartrate, such as hydrocodone bitartrate hemipentahydrate.

Hydrocodone is a semi-synthetic opioid that may be derived from codeine. Hydrocodone may be administered orally as an analgesic to treat moderate to severe pain and an antitussive to treat cough. Typically, hydrocodone is administered in the form of hydrocodone bitartrate.

The formation of hydrocodone salts by addition of an acid to hydrocodone is known.

US 2013/0035488 discloses the formation of hydrocodone salts by stepwise addition of an acid to hydrocodone. However, either the products directly obtained by these methods are non-flowable and therefore difficult to use for manufacturing, or the process is slow, labour intensive, and inefficient.

We have now found a new and efficient process for the production of salts of hydrocodone, which are easy to handle and formulate into pharmaceutical compositions.

The listing or discussion of an apparently prior-published document in this specification should not necessarily be taken as an acknowledgement that the document is part of the state of the art or common general knowledge.

In a first aspect of the invention, there is provided a process for the formation of hydrocodone bitartrate, which process comprises the steps:
(i) providing a solution comprising hydrocodone and a first portion of tartaric acid;
(ii) adjusting the temperature of the solution to less than about 50° C. and forming a precipitate comprising a tartaric acid salt of hydrocodone from said solution; and
(iii) adding a second portion of tartaric acid to the product formed in step (ii).

This process is hereinafter referred to as the "process of the invention".

The compounds employed in, or the products of, the processes described herein may also contain one or more asymmetric carbon atoms and may therefore exist as enantiomers or diastereoisomers, and may exhibit optical activity. The process of the invention thus encompasses the use or production of such compounds (or salts) in any of their optical or diastereoisomeric forms, or in mixtures of any such forms. In particular, the tartaric acid used in step (i) and step (iii) may be selected from D-(−)-tartaric acid, L-(+)-tartaric acid, DL-tartaric acid or meso-tartaric acid, or a mixture thereof. In a preferred embodiment of the process of the invention, the tartaric acid in step (i) and step (iii) is (predominantly) L-(+)-tartaric acid.

In one embodiment of the process of the invention, the hydrocodone used in step (i) is the freebase of hydrocodone. In another embodiment, the hydrocodone used in step (i) is a salt of hydrocodone, for example an inorganic or mineral acid salt or an organic acid salt of hydrocodone, such as a hydrochloric, phosphoric, tartaric or acetic acid salt of hydrocodone. Preferably, the hydrocodone is a tartaric acid salt of hydrocodone or, more preferably, the freebase of hydrocodone.

Solvents may be employed in the process of the invention. Suitable solvents for use in the process of the invention include alcohols (such as methanol, ethanol, propanol and butanol), water, acetonitrile, dioxane, alkanes (such as pentane, hexane, heptane and petroleum ethers), furans (such as tetrahydrofuran and 2-methyltetrahydrofuran), halogenated solvents (such as dichloromethane, trichloromethane, and dibromoethane), aromatic solvents (such as benzene, toluene and xylene), ketones (such as acetone and butanone), ethers (such as methyl ethyl ether, diethyl ether and butyl methyl ether) and esters (such as methyl acetate, ethyl acetate, propyl acetate and butyl acetate), and mixtures thereof.

The solution provided in step (i) of the process of the invention, may comprise one or more (e.g. one, two or three) solvents. In an embodiment of the process of the invention, the solution provided in step (i) comprises an alcohol (e.g. ethanol) or a mixture of alcohols (e.g. methanol and ethanol). In another embodiment, the solution provided in step (i) comprises water. In a further embodiment, the solution provided in step (i) comprises an alcohol and water (e.g. ethanol and water) or a mixture of alcohols and water (e.g. methanol, ethanol and water).

In another embodiment, the solution provided in step (i) comprises ethanol and water wherein the ethanol is present at from about 70% to about 95% (such as from about 80% to about 90%) by weight of the combined weight of ethanol and water in the solvent.

The term "weight ratio" as used herein means the ratio of the weight of a first substance to the weight of a second substance (or mixture of substances). For the avoidance of any doubt, the term "weight ratio" does not take into consideration any additional matter present in the system, e.g. reaction material.

The skilled person will appreciate that the term "about", as used herein (for example in the context of amounts (e.g. stoichiometric or weight ratios), time periods and/or temperatures) is intended to refer to variables that are approximate and as such may vary by ±20%, ±10%, ±5%, ±2% or ±1% from the values specified herein.

In step (i) of the process of the invention, a solution is provided comprising hydrocodone and a first portion of tartaric acid.

By the use of the terms "first portion" and "second portion" it is meant that the tartaric acid is provided in two discrete and separable portions, i.e. the totality of the tartaric acid is not merely added in one single addition.

In one embodiment, the molar ratio of hydrocodone to the first portion of tartaric acid is from about 1:0.2 to about 1:0.8, such as from about 1:0.3 to about 1:0.7, for example from about 1:0.4 to about 1:0.65. In a preferred embodiment, the molar ratio of hydrocodone to the first portion of tartaric acid is from about 1:0.5 to about 1:0.6.

The term "molar ratio" as used herein means the ratio of the number of moles of a first substance to the number of moles of a second substance. For the avoidance of any doubt, the term "molar ratio" does not indicate the absolute number of moles of a substance present in the reaction mixture.

Step (i) of the process of the invention may further comprise the step of warming the solution. In one embodiment of the invention, the temperature of the solution is increased to a temperature of from about 50° C. to about 90° C., preferably from about 60° C. to about 70° C., more preferably to about 65° C. The person skilled in the art will understand that increasing the temperature of the solution will aid the dissolution of the hydrocodone and the tartaric acid in the solution.

In one embodiment of the process of the invention, the solution provided in step (i) is substantially free of solid hydrocodone and/or tartaric acid.

The person skilled in the art will understand that "substantially free of solid hydrocodone and/or tartaric acid" means that at least 50%, 60%, 70%, 80%, 90%, 95%, such as at least 99% by weight of the hydrocodone, the tartaric acid and/or the tartaric acid salts of hydrocodone are dissolved in the solution, i.e. less that 50%, 40%, 30%, 20%, 10%, 5%, such as less than 1% by weight of all forms of hydrocodone and/or tartaric acid are in the solid state in the mixture.

In another embodiment of the invention, step (i) further comprises a step of filtering the solution. In a preferred embodiment, the solution is filtered by polish filtration. In a more preferred embodiment, the solution is filtered by hot polish filtration.

In a particular embodiment of step (i) of the invention, the molar ratio of hydrocodone to the first portion of tartaric acid is from about 1:0.3 to about 1:0.7 and the solution comprises one or more alcohols (e.g. one or two) and/or water. In another embodiment, said solution comprises ethanol and water. In another embodiment, the molar ratio of hydrocodone to the first portion of tartaric acid is from about 1:0.5 to about 1:0.6 and the solution comprises ethanol and water.

In a preferred embodiment of step (i) of the process of the invention, the solution provided in step (i) comprises the freebase of hydrocodone, tartaric acid, ethanol and water, wherein the molar ratio of hydrocodone to tartaric acid is from about 1:0.5 to about 1:0.6 and wherein the weight ratio of ethanol to water is from about 4:1 to about 9:1.

Step (ii) of the process of the invention comprises adjusting the temperature of the solution obtained in step (i) to be less than about 50° C. and forming precipitate of a tartaric acid salt of hydrocodone.

In an embodiment of the process of the invention, the precipitate formed in step (ii) comprises from about 5% to about 95% by weight of the total hydrocodone in the system, such as from about 30% to about 90%, for example from about 50% to about 90% or from about 60% to about 80%.

In another embodiment of the process of the invention, the precipitate formed in step (ii) comprises predominantly hydrocodone tartrate (e.g. wherein the precipitate formed in step (ii) comprises greater than 50% by weight hydrocodone tartrate).

For the avoidance of doubt, by the use of the word "precipitation" or the phrase "forming a precipitate", we mean that a dissolved substance is converted into its solid, unsolubilised form. The term "precipitate" refers to the solid that is formed. Precipitation may occur when the concentration of a substance in a solution sufficiently exceeds the limit of solubility in that solution. The person skilled in the art will be aware of a variety of processes and conditions that bring about precipitation. Such processes and conditions include, but are not limited to, cooling a solution, evaporating a portion of the solvent (or otherwise causing a reduction in the effective volume of a solvent) from the solution, or adding a different solvent (e.g. an antisolvent). Additionally, precipitation may be triggered by the introduction of nucleation sites. Nucleation may be facilitated by, for example, "seeding" a solution, e.g. using the desired product in solid (typically crystalline) form. Further methods by which precipitation of the tartaric acid salt of hydrocodone may be facilitated include concentration of the solution of tartaric acid and hydrocodone. This may be achieved by removal of the solvent, e.g. by distillation. Precipitation may be caused by these or other methods either alone or in combination, e.g. by simultaneously seeding and cooling a solution. A particularly preferred method for facilitating precipitation of the tartaric acid salt of hydrocodone is seeding.

Step (ii) of the process of the invention involves adjusting the temperature of the solution to be less than about 50° C. By this, it is meant that the temperature is adjusted to be less than 50.5° C.

In one embodiment of step (ii) of the process of the invention, the solution obtained in step (i) is cooled (so as to precipitate the tartaric acid salt of hydrocodone). The temperature of the solution may be adjusted (e.g. cooled) to less than about 40° C. or preferably less than about 30° C., e.g. to about 0° C., preferably to about 10° C., more preferably to about 20° C., most preferably to about 30° C. In an embodiment of step (ii) of the process of the invention, the temperature of the solution obtained in step (i) may be adjusted to be from about 0° C. to about 40° C. The process of cooling the solution obtained in step (i) can be used to bring about the precipitation of the tartaric acid salt of hydrocodone in a controlled and predictable manner.

In a particular embodiment of the process of the invention, the temperature adjustment step is completed before any further tartaric acid (e.g. the tartaric acid in step (iii)) is added. In an embodiment of step (ii) of the process of the invention, the temperature of the solution is cooled to a temperature of about 30° C. or less (e.g. from about 65° C.). Reduction of the temperature of the solution of step (i) may induce precipitation of the tartaric acid salt of hydrocodone so as to form a slurry (e.g. a free-flowing slurry).

Accordingly, in an embodiment of the process of the invention, the tartaric acid salt of hydrocodone precipitated in step (ii) is obtained in the form of a free-flowing slurry.

The term "free-flowing slurry", and the properties of such a product, will be understood by the person skilled in the art. By the use of the term "free-flowing slurry" it is meant that the product is a mixture of solid particles in a liquid, wherein the overall mixture is, for example, capable of flowing under gravity and/or capable of being pumped. Alternatively, or additionally, the solid and liquid components of the free-flowing slurry may be readily separated by filtration (e.g. vacuum filtration or gravity filtration).

In chemical manufacturing processes, it may be advantageous to obtain a mixture of solid particles in a liquid that is free-flowing as such a mixture is substantially easier to process than a non-free-flowing mixture of solid particles in a liquid, for example it may be easier to transport, mix, separate, purify and/or filter the free-flowing product.

Unless otherwise specified, when used herein, the term "free-flowing slurry" includes, but is not limited to, a suspension of a solid (e.g. wherein the solid is a tartaric acid salt of hydrocodone) in a liquid, such as a solvent, which suspension has a bulk density of from about 0.60 g/ml to about 0.70 g/ml.

In one embodiment of the invention, the tartaric acid salt of hydrocodone precipitated in step (ii) has a bulk density of from about 0.60 g/ml to about 0.70 g/ml. If the product of step (ii) has a bulk density of from about 0.60 g/ml to about 0.70 g/ml then the product is to be considered to be a free-flowing slurry; however, for the avoidance of doubt, the precipitate may still be considered to be free-flowing even if it does not have a bulk density of from about 0.60 g/ml to about 0.70 g/ml.

In an additional embodiment of the invention, the product of step (ii) is a mixture comprising the precipitated tartaric acid salt of hydrocodone wherein the mixture has a bulk density of from about 0.60 g/ml to about 0.70 g/ml, preferably from about 0.62 g/ml to about 0.68 g/ml, more preferably about 0.65 g/ml. In a more particular embodiment, the mixture comprising the precipitated tartaric acid salt of hydrocodone has a bulk density of less than about 0.70 g/ml or less than about 0.68 g/ml.

Methods for determination of the bulk density will be known to the person skilled in the art, but include those methods as set out in the OECD Guidelines for the Testing of Chemicals, Section 1, Test no. 109: Density of Liquids and Solids.

Alternatively, when used herein, the term "free-flowing slurry" includes, but is not limited to, a suspension of a solid (e.g. wherein the solid is a tartaric acid salt of hydrocodone) in a liquid, such as a solvent, in which the particle size distribution of the solid particles is sufficiently small to enable the slurry to be free flowing.

In one embodiment, the product of step (ii) comprises precipitated tartaric acid salt of hydrocodone in which at least 10% by volume of the particles of the tartaric acid salt of hydrocodone have a diameter of less than about 50 μm, preferably less than about 20 μm. In a further embodiment, at least 10% by volume of the particles have a diameter of less than about 10 μm (e.g. less than about 7 μm). The above particle sizes may also alternatively apply in respect of the product obtained after step (iii).

In a further embodiment, the product of step (ii) comprises precipitated tartaric acid salt of hydrocodone in which at least 50% by volume of the particles of the tartaric acid salt of hydrocodone have a diameter of less than about 500 μm, preferably less than about 200 μm. In a further embodiment, at least 50% by volume of the particles have a diameter of less than about 100 μm (e.g. less than about 75 μm). The above particle sizes may also alternatively apply in respect of the product obtained after step (iii).

In a still further embodiment, the product of step (ii) comprises precipitated tartaric acid salt of hydrocodone in which at least 90% by volume of the particles of the tartaric acid salt of hydrocodone have a diameter of less than about 5000 μm, preferably less than about 2000 μm. In a further embodiment, at least 90% by volume of the particles have a diameter of less than about 1000 μm (e.g. less than about 750 μm). The above particle sizes may also alternatively apply in respect of the product obtained after step (iii).

In a preferred embodiment, the product of step (ii) comprises precipitated tartaric acid salt of hydrocodone in which at least 80% by volume of the particles of the tartaric acid salt of hydrocodone have a diameter that is from about 0.5 μm to about 2000 μm, preferably from about 1 μm to about 1000 μm, such as from about 3 μm to about 700 μm.

It is preferred that the above-mentioned particle size distributions apply when the particle size distribution is determined according to laser diffraction techniques, for example as hereinafter defined.

Alternative methods for determination of the "particle size distribution" will be known to the person skilled in the art.

In one embodiment of the invention, the tartaric acid salt of hydrocodone precipitated in step (ii) has one or both of the following properties:

(a) a bulk density of from about 0.60 g/ml to about 0.70 g/ml; and (b) at least 80% by volume of the particles of the tartaric acid salt of hydrocodone have a diameter that is from about 0.5 μm to about 2000 μm.

In a further embodiment of the invention, the tartaric acid salt of hydrocodone precipitated in step (ii) has none of the properties (a) and (b) above. If the product of step (ii) satisfies one or both of the properties (a) and (b) then the product is to be considered to be a free-flowing slurry; however, for the avoidance of doubt, the precipitate may still be considered to be free-flowing even if it does not satisfy either of the properties (a) and (b).

Step (iii) of the process of the invention comprises adding a second portion of tartaric acid to the product formed in step (ii).

In an embodiment of step (iii) of the process of the invention, the molar ratio of hydrocodone in the system to the second portion of tartaric acid is from about 1:0.2 to about 1:0.8, such as from about 1:0.4 to about 1:0.7, for example from about 1:0.45 to about 1:0.65. In a preferred embodiment, the molar ratio of hydrocodone in the system to the second portion of tartaric acid is from about 1:0.5 to about 1:0.6.

In another embodiment, the molar ratio of hydrocodone in the system to the total amount of tartaric acid used in step (i) and step (iii) is from about 1:0.9 to about 1:1.2, such as from about 1:1 to about 1:1.15. In a particular embodiment, the molar ratio of hydrocodone in the system to the total amount of tartaric acid used in step (i) and step (iii) is from about 1:1.05 to about 1:1.1.

In step (iii) of the process of the invention, the second portion of tartaric acid may be dissolved in a solvent before it is added to the product formed in step (ii). The solvent may comprise any of those listed previously as suitable solvents for use in the process of step (i). The solvent may comprise one or a mixture of two of more (e.g. one, two or three) solvents. In one embodiment, the solvent may comprise an alcohol (e.g. ethanol or methanol) or a mixture of alcohols (e.g. ethanol and methanol). In another embodiment, the solvent may comprise water. In a further embodiment, the solvent may comprise an alcohol (e.g. ethanol or methanol) and water, or a mixture of alcohols (e.g. ethanol and methanol) and water. In a particular embodiment, the solvent comprises a mixture of ethanol, water and methanol wherein the ethanol is present at from about 60 to about 95% (such as from about 70 to about 90%, preferably from about 80 to about 85%) by weight of the combined weight of ethanol, water and methanol in the solvent. In another particular embodiment, the solvent comprises a mixture of ethanol, water and methanol wherein the water is present at from about 5 to about 30% (such as from about 7 to about 20%, preferably from about 10 to about 15%) by weight of the combined weight of ethanol, water and methanol in the solvent. In a further particular embodiment, the solvent comprises a mixture of ethanol, water and methanol wherein the methanol is present at from about 2 to about 15% (such as from about 3 to about 10%, preferably from about 4 to about 7%) by weight of the combined weight of ethanol, water and methanol in the solvent.

In another embodiment, the second portion of tartaric acid is dissolved in a solvent (or mixture of solvents), which is then filtered, e.g. polish filtered, prior to being added to the product of step (ii).

In a further embodiment of step (iii) of the process of the invention, the second portion of tartaric acid is added (preferably continuously added) to the product formed in step (ii) over a period of at least about 0.25 hours, e.g. from about 0.25 hours to about 24 hours, such as from about 1 hour to about 8 hours, for example from about 2 hours to about 4 hours. In a particular embodiment, in step (iii), the second portion of tartaric acid is added to the product formed in step (ii) over a period of about 4 hours.

In one embodiment of step (iii) of the process of the invention, the second portion of tartaric acid is added at an approximately continuous rate (i.e. it is added continuously) to the product formed in step (ii). For example, the second portion of tartaric acid may be added at an approximately continuous rate over a period of at least 1 minute (preferably at least 0.25 hours, e.g. from about 0.25 hours to about 24 hours, from about 1 hour to about 8 hours, or, most particularly, from about 2 hours to about 4 hours). By the use of the terms "continuous rate" and "continuously", it is included that the second portion of tartaric acid may be added dropwise provided the rate of addition remains approximately constant. In this way, continuous addition may be dropwise addition provided that the interval between successive dropwise additions does not exceed approximately one minute.

In particular embodiments of the invention that involve continuous addition of the second portion of tartaric acid, the second portion of tartaric acid comprises from about 0.2 to about 0.8 molar equivalents (such as from about 0.4 to about 0.7) molar equivalents relative to the hydrocodone.

In another particular embodiment of step (iii) of the process of the invention, the mixture is held at a temperature of less than or equal to 50° C. (e.g. less than or equal to 40° C.) immediately prior to the addition of the second portion of tartaric acid.

In an embodiment of step (iii) of the process of the invention, the temperature of the mixture comprising the product of step (ii) is increased during the addition of the second portion of tartaric acid. In such an embodiment, the temperature may be increased to a temperature of from about 40° C. to about 80° C., such as from about 50° C. to about 70° C. In a particular embodiment, the temperature of the mixture comprising the product of step (ii) is increased to a temperature of from about 52° C. to about 60° C. during the addition of the second portion of tartaric acid In an embodiment of the process of the invention, the process comprises an additional step of reducing the temperature of the product of step (iii). In a particular embodiment, the temperature of the mixture obtained in step (iii) is reduced to from about −10° C. to about 30° C., such as to from about 0° C. to about 20° C. after the addition of the second portion of the tartaric acid. In a particular embodiment, the temperature of the mixture is reduced to about 10° C. In a further embodiment, after the additional step of reducing the temperature of the product obtained in step (iii), the mixture is held at the reduced temperature for from about 30 minutes to about 8 hours, such as about 1 hours to about 4 hours, for example from about 1.5 hours to about 3 hours. In a particular embodiment, the mixture is held at the reduced temperature for about 2 hours.

In another embodiment of the invention, the process comprises an additional step of isolating the hydrocodone bitartrate from the product obtained in step (iii). In one embodiment, this isolation step is achieved using filtration, and optionally comprises a further step of washing or reslurrying the solid hydrocodone bitartrate with a solvent or a solvent mixture. Particular solvents that may be used in such processes include ketones (e.g. acetone or butatone) or mixtures of ketones with other solvents. Particular solvents and solvent mixtures that may be mentioned include ethanol, water, acetone and a mixture of acetone and water. Where the solvent that is used in the reslurrying process is a solvent mixture comprising acetone and water, preferably the ratio of acetone to water in the solvent mixture is from 10:1 to 20:1 by weight (preferably about 15:1 by weight).

In another embodiment, the isolation step further optionally comprises the step of reslurrying the solid hydrocodone bitartrate with a solvent or solvent mixture, such as ethanol, water, acetone or, preferably, a mixture of acetone and water. The combined processes of filtering and reslurrying may be carried out a number of times (such as one, two, three, four, five, or six times). In one embodiment, the reslurrying step is carried out once. In another embodiment, the reslurrying step is carried out twice (with each reslurrying being separated by a filtration step). Without wishing to be bound by theory, the step of reslurrying the solid hydrocodone bitartrate may aid the removal of residual solvent, such as ethanol, and thereby facilitate the drying of the solid hydrocodone bitartrate.

In a particular embodiment of step (iii) of the process of the invention, the molar ratio of hydrocodone in the system to the second portion of tartaric acid is from about 1:0.4 to about 1:0.7 and the tartaric acid is dissolved in a solvent before it is added to the product formed in step (ii), wherein said solvent comprises one or more alcohols (e.g. one or two) and water. In another embodiment, said solvent comprises ethanol, methanol and water. In another embodiment, the molar ratio of hydrocodone in the system to the second portion of tartaric acid is from about 1:0.5 to about 1:0.6 and the tartaric acid is dissolved in a solvent before it is added to the product formed in step (ii), wherein said solvent comprises one or more alcohols (e.g. one or two) and water. In another embodiment, the molar ratio of hydrocodone in the system to the second portion of tartaric acid is from about 1:0.5 to about 1:0.6 and the tartaric acid is dissolved in a solvent before it is added to the product formed in step (ii), wherein said solvent comprises ethanol, methanol and water.

In a preferred embodiment of step (iii) of the process of the invention, the second portion of tartaric acid is dissolved in a solvent comprising ethanol, methanol and water, wherein the molar ratio of hydrocodone in the system to the second portion of tartaric acid is from about 1:0.5 to about 1:0.6. The solution comprising the second portion of tartaric acid is then polish filtered at ambient temperature prior to its continuous addition over a period of about 4 hours, to the product formed in step (ii). During this addition, the temperature of the mixture comprising the hydrocodone is raised to a temperature of from about 52° C. to about 60° C. The mixture is cooled to about 10° C. and is maintained at this temperature for a period of about 2 hours.

Unless otherwise specified, as used herein, the term "ambient temperature" may refer to the temperature of the surroundings and, as such, may also be referred to as room temperature. Such temperatures may typically be about 20° C. In particular, the reference to a reaction being performed at "ambient" or "room" temperature indicates that the reaction is performed in the absence of any external heating or cooling In a further embodiment of the invention, the hydrocodone bitartrate may be isolated from the product of step (iii), for example, by any process known to the skilled person. Such isolation processes include filtration, decantation, evaporation of the solvent, and combinations thereof.

In an embodiment of the first aspect of the invention, the hydrocodone bitartrate that is formed as a result of the process is hydrocodone bitartrate hemipentahydrate.

The processes disclosed herein are advantageous in that the product of step (ii) is obtained as a free-flowing slurry of a hydrocodone salt. Furthermore, such a process allows for the purification of the solution comprising the intermediate acid salt of hydrocodone by filtration e.g. polish filtration, to increase the purity of the final product. In some embodiments, continuous addition of a portion of the acid to the solution simplifies the process and greatly facilitates scale up.

The processes disclosed herein are also advantageous in that the temperature adjustment (e.g. cooling) in step (ii) may bring about the formation of a precipitate of a hydrocodone salt in a controlled manner. The formation of a precipitate at this stage may allow the addition of the second portion of the tartaric acid in a continuous manner while minimising the risk of flash precipitation occurring. This greatly facilitates large scale manufacture of the final hydrocodone bitartrate product.

In a further embodiment of the first aspect of the invention, the process is a large scale manufacturing process. For example, total amount of hydrocodone present after step (i) may be at least 1 kg, at least 5 kg. Preferably the total amount of hydrocodone present after step (i) is at least 10 kg, or is at least 50 kg. Most preferably it is at least 100 kg.

According to a second aspect of the invention, there is provided a process for the formation of a pharmaceutical composition comprising hydrocodone bitartrate which process comprises the steps:
(a) obtaining hydrocodone bitartrate by a process of the invention; and
(b) bringing into association the hydrocodone bitartrate so obtained with one or more pharmaceutically acceptable excipients, diluents or carriers.

In an embodiment of the second aspect of the invention, the hydrocodone bitartrate is purified (e.g. isolated) prior to being brought into association with the one or more pharmaceutically acceptable excipients, diluents or carriers.

The skilled person will understand the steps required to formulate the pharmaceutical composition, and the pharmaceutically acceptable excipients, diluents and carriers which may be employed.

Examples of excipients (such as fillers, binders, disintegrants, coatings and lubricants) suitable for use in the second aspect of the invention include polyvinylpyrrolidone (PVP), cellulose and modified cellulose (such as microcrystalline cellulose, hydroxypropyl cellulose, hydroxypropyl methylcellulose (HPMC), carboxymethyl cellulose), mannitol, corn starch, potato starch, polyethylene, polyvinyl alcohol, polyvinyl acetate, sodium stearyl fumarate, magnesium stearate and talc.

The pharmaceutical composition may comprise from about 1 µg to about 500 mg of hydrocodone, such as from about 500 µg to about 100 mg, for example from about 800 µg to about 50 mg, i.e. from about 1 mg to 20 mg per single dose. In one embodiment of the second aspect of the invention, the pharmaceutical composition additionally comprises paracetamol (acetaminophen) and/or ibuprofen.

The pharmaceutical composition may be formulated for administration, for example, orally (as, for example, a tablet, syrup or lozenge), topically (e.g. a patch) or parenterally (i.e. by injection).

According to a third aspect of the invention, there is provided a mixture of hydrocodone bitartrate and a solvent obtainable by the process as defined in the first aspect of the invention or any embodiment or combination of embodiments thereof. Preferably the mixture is in the form of a free flowing slurry.

In a first embodiment of the third aspect of the invention, the mixture of hydrocodone bitartrate and solvent obtainable by said process is a mixture of hydrocodone bitartrate hemipentahydrate and solvent.

In a further embodiment of the third aspect of the invention, the mixture contains a substantial quantity of hydrocodone bitartrate, e.g. at least 1 kg, or preferably at least 5 kg or more preferably at least 10 kg (such as at least 50 kg, or at least 100 kg).

According to a fourth aspect of the invention, there is provided a pharmaceutical composition comprising hydrocodone bitartrate (e.g. hydrocodone bitartrate hemipentahydrate) obtained by a process as defined in the first aspect of the invention or any embodiment or combination of embodiments thereof.

Preferences and options for a given aspect, feature or parameter of the invention should, unless the context indicates otherwise, be regarded as having been disclosed in combination with any and all preferences and options for all other aspects, features and parameters of the invention.

Particle Size Analysis

The following is a description of a method for particle size analysis using laser diffraction. Any conventional laser diffraction particle size analyser may be used, and the procedure and parameters detailed below are appropriate for a Malvern Mastersizer 2000 analyser.

Sample Preparation

Prepare a dispersant solution by adding 2.0 mL of a dispersant (such as Span® 85 (Fisher Scientific) or Miglyol 812) to 1 L of n-hexane and mix well.

Weigh 25 mg (+/−2.5 mg) sample material directly into a tared 20-mL glass scintillation vial. Add 15 mL of the dispersant solution, and swirl to mix then sonicate for 4 minutes.

The sample may be sonicated for more than 4 minutes if material appeared as lumps in the dispersant.

Laser Diffraction Analysis

Parameters

Instrument conditions should be set as appropriate for the test material and dispersant used in the analysis. Suitable parameters to use when analysing hydrocodone bitartrate dispersed in Span 85® are suggested in the table below.

| Parameter | Value |
| --- | --- |
| Dispersant RI | 1.370 |
| Particle RI, Absorption | 1.675, 0.1 |
| Pump Speed | 3000 rpm |
| Sonication | None (See above for sonication requirement prior to sample introduction into the dispersant) |
| Pre-measurement Delay | 2.0 Minutes |
| Measurement Time | 20 Seconds (20000 snaps) |
| Background Time | 20 Seconds (20000 snaps) |
| Delay between measurement | 10 Seconds |
| Obscuration Limits | Lower 10% and Upper 30% |

Sample Analysis

Analyse the sample(s) per the method parameters listed above. Note that the sample must be introduced into the sample dispersion unit immediately after the completion of sonication. Pour the entire contents of the sample vial into the sample dispersion unit, rinse the vial with approximately 2 mL of dispersant solution and pour this solution into the sample dispersion unit.

Obscuration Evaluation

If the obscuration is less than 5%, stop the analysis, drain, clean, and refill the sample dispersion unit. Repeat the sample preparation procedure with an increased amount of sample material. If the obscuration exceeds 15%, slowly add dispersant solution until the obscuration is within the specified range.

Calculations

Particle size distribution values (including D(0.1), D(0.5) and D(0.9) values) are then generated from the laser diffraction data according to standard analytical procedures.

The invention is illustrated by the following examples in which:

FIG. 1 shows a particle size distribution curve for the product of Example 5a.

FIG. 4 shows a particle size distribution curve for the product of Example 6a.

EXAMPLES

Example 1

Figure 1:
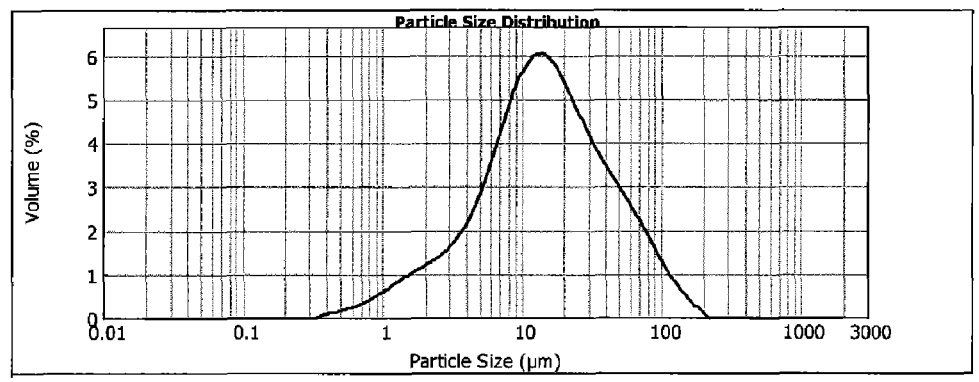

Preparation of a Free-Flowing Slurry of Hydrocodone Bitartrate Hemipentahydrate

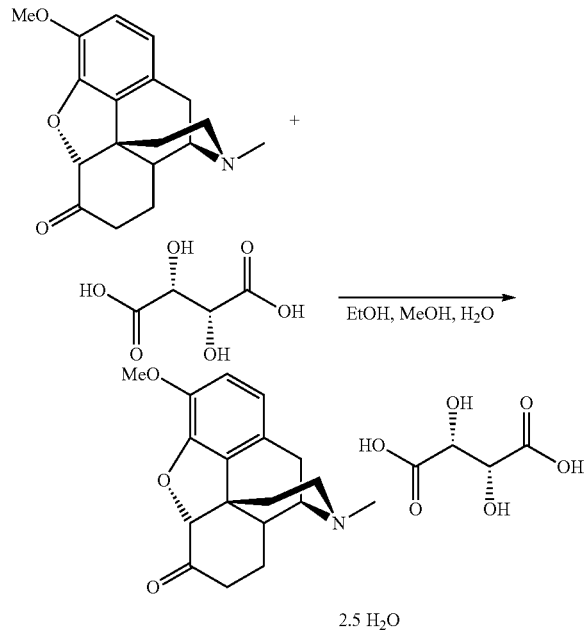

Hydrocodone free-base (636.8 g, 2.127 mol) and L-(+)-tartaric acid (159.6 g, 1.063 mol, 0.5 eq.) were dissolved in EtOH (3768 g, 4776 mL) and water (701 g, 701 mL), and the resulting mixture was heated to about 65° C. The solution was hot polish filtered (5 μm filter) and rinsed with EtOH/water and then EtOH/MeOH. The solution was cooled to about 30° C. to induce precipitation of a tartrate salt of hydrocodone in the form of a thin slurry. In another vessel L-(+)-tartaric acid (191.5 g, 1.276 mol) was dissolved in water (159.2 g, 159.2 mL), EtOH (1068 g, 1353 mL) and MeOH (63.0 g, 79.6 mL) and polish filtered at ambient temperature. This tartaric acid solution was slowly added to the slurry over about 4 hr. As the tartaric acid solution was added to the slurry, the temperature was increased to about 60° C. and then held for about 1 hr at about 60° C. after the addition was completed. The slurry was cooled at a rate of 5° C./hr to 10° C. and held for about 2 hr at 10° C.

Example 2

Isolation of Hydrocodone Bitartrate Hemipentahydrate

The slurry of hydrocodone bitartrate hemipentahydrate obtained in Example 1 was filtered. The solid was washed twice with ethanol and dried under reduced pressure (about 78 kPa) at about 20° C. for 24 hr. The solid was purged with wet nitrogen at 20° C. for 24 hr after which it was dried a second time under reduced pressure (about 78 kPa) at about 20° C. for 24 hr. This resulted in hydrocodone bitartrate hemipentahydrate as an off white crystalline solid (1031.6 g, 98%).

Example 3

Preparation of a Free-Flowing Slurry of a Hydrocodone Bitartrate Hemipentahydrate (Ethanol Reslurry)

Hydrocodone free-base (25.3 kg, 76.5 mol, 90% assay) and L-(+)-tartaric acid (5.8 kg, 38.6 mol, 0.5 eq.) were dissolved in EtOH (135.8 kg) and water (24.7 kg), and the resulting mixture was heated to about 65° C. The solution was hot polish filtered (5 μm filter) and rinsed with EtOH (26.7 kg)/water (3.3 kg) and then EtOH (30.0 kg)/MeOH (11.7 kg). The solution was hot polish filtered (5 μm filter). The combined solution was cooled to about 25° C. to induce precipitation of a tartrate salt of hydrocodone in the form of a thin slurry. In another vessel L-(+)-tartaric acid (6.9 kg, 45.9 mol, 0.6 eq.) was dissolved in water (5.8 kg), EtOH (38.7 kg) and MeOH (2.4 kg). This tartaric acid solution was slowly added to the slurry through a polish filter (5 μm filter) at ambient temperature over about 4 hr. As the tartaric acid solution was added to the slurry, the temperature was increased to 55° C. The slurry was held 1 hr at about 55° C. and cooled to about 10° C. over about 6 hr and held for about 2 hr at about 10° C. and filtered. The solid was reslurried twice with ethanol (62.1 kg) and dried under reduced pressure (about −10 psig) at about 20° C. for 24 hr. The solid was purged with wet nitrogen at 20° C. for 24 hr. This resulted in hydrocodone bitartrate hemipentahydrate as an off white crystalline solid (35.2 kg, 93%).

Example 4

Preparation of a Free-Flowing Slurry of a Hydrocodone Bitartrate Hemipentahydrate (Acetone/Water Reslurry)

Hydrocodone free-base (19.6 kg, 58.3 mol, 89% assay) and L-(+)-tartaric acid (4.4 kg, 29.2 mol, 0.5 eq.) were dissolved in EtOH (103.6 kg) and water (19.1 kg), and the resulting mixture was heated to about 65° C. The solution was hot polish filtered (5 μm filter). To the reactor was charged EtOH (43.1 kg), MeOH (8.6 kg), and water (2.6 kg) and heated to about 50° C. The solution was hot polish filtered (5 μm filter). The combined solution was cooled to about 25° C. to induce precipitation of a tartrate salt of hydrocodone in the form of a thin slurry. In another vessel L-(+)-tartaric acid (5.3 kg, 35.0 mol, 0.6 eq.) was dissolved in water (4.2 kg), EtOH (29.5 kg) and MeOH (1.7 kg). This tartaric acid solution was slowly added to the slurry through a polish filter (5 μm filter) at ambient temperature over about 4 hr. As the tartaric acid solution was added to the slurry, the temperature was held at about 30° C. The slurry was held for about 1 hr at about 30° C. and cooled to about 5° C. over about 4 hr and held for about 2 hr at about 5° C. and filtered. The solid was reslurried twice in acetone (131.9 kg)/water (8.8 kg) and dried under reduced pressure (about −10 psig) at about 20° C. for 24 hr. The solid was purged with wet nitrogen at 20° C. for 24 hr. This resulted in hydrocodone bitartrate hemipentahydrate as an off white crystalline solid (26.7 kg, 92%).

Example 5

The product of Example 4 was obtained in triplicate (Examples 5a to 5c) and subjected to particle size analysis using a Malvern Mastersizer 2000 analyser according to the process outlined above.

The dispersant used was Miglyol 812, and the instrument parameters were set as follows.

| Parameter | Value |
|---|---|
| Dispersant | Miglyol 812 |
| Dispersant RI | 1.450 |
| Particle RI, Absorption | 1.663, 0.1 |
| Pump Speed | 2000 (±10%) rpm |
| Sonication | 10 minutes prior to sample addition to instrument |
| Pre-measurement Delay | 2.0 Minutes |
| Measurement Time | 12 Seconds (12000 snaps) |
| Background Time | 12 Seconds (12000 snaps) |
| Delay between measurement | 60 Seconds |
| Obscuration Limits | Lower 5% and Upper 15% |

The following particle size data were obtained for these products.

| Sample | D (0.1) μm | D (0.5) μm | D (0.9) μm | Residual | % Obscuration |
|---|---|---|---|---|---|
| Example 5a | 3.165 | 14.475 | 58.817 | 0.164 | 8.12 |
| Example 5b | 6.608 | 72.361 | 698.343 | 0.911 | 5.77 |
| Example 5c | 2.201 | 6.932 | 456.24 | 0.389 | 13.78 |

Observations:

The amount of sample weighed for each of the above samples was similar, however the % obscuration varied from 6-50%. The entire sample was added to the instrument and if the obscuration was too high then more Miglyol was added.

Figure 2:
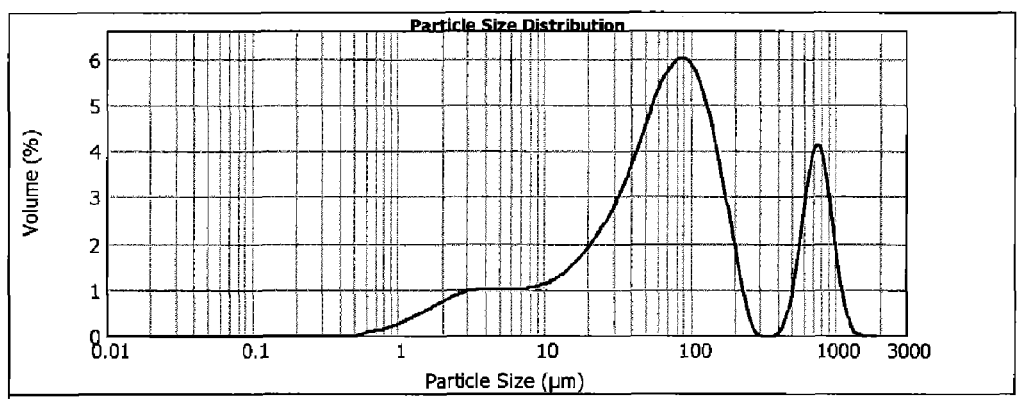
FIG. 2 shows a particle size distribution curve for the product of Example 5b.
Figure 3:
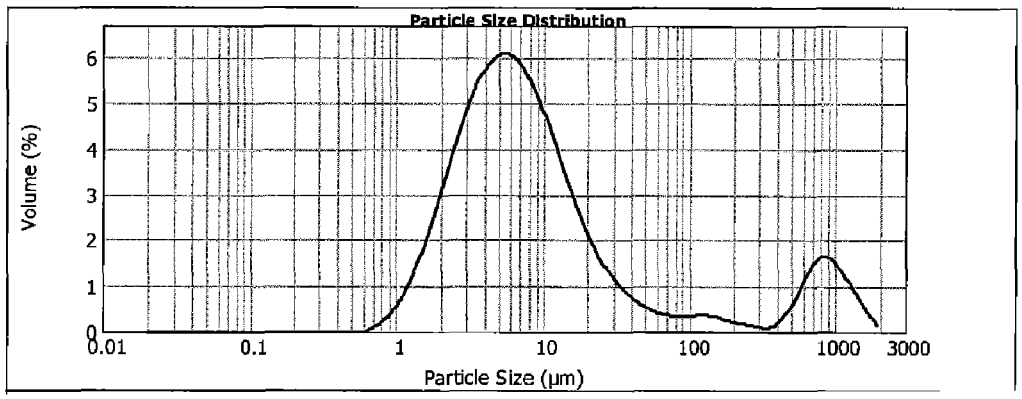
FIG. 3 shows a particle size distribution curve for the product of Example 5c.

Particle size distribution curves for Examples 5a, 5b and 5c are shown in FIGS. 1, 2 and 3, respectively.

Example 6

Two further samples of a product obtained according to the process of Example 4 were produced and subsequently comilled (delumped) using a comill (Examples 6a and 6b).

The products obtained by this process were subjected to particle size analysis according to the process outlined above in respect of Example 5.

The following particle size data were obtained for these products.

| Sample | D (0.1) μm | D (0.5) μm | D (0.9) μm | Residual | % Obscuration |
|---|---|---|---|---|---|
| Example 6a | 2.731 | 18.446 | 91.584 | 0.546 | 8.31 |
| Example 6b | 4.867 | 50.417 | 147.282 | 0.321 | 10.72 |

Figure 4:
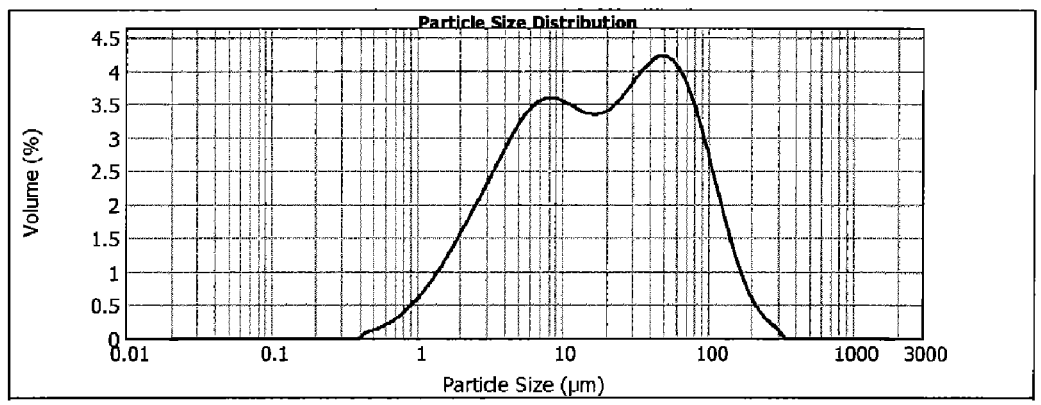
Figure 5:
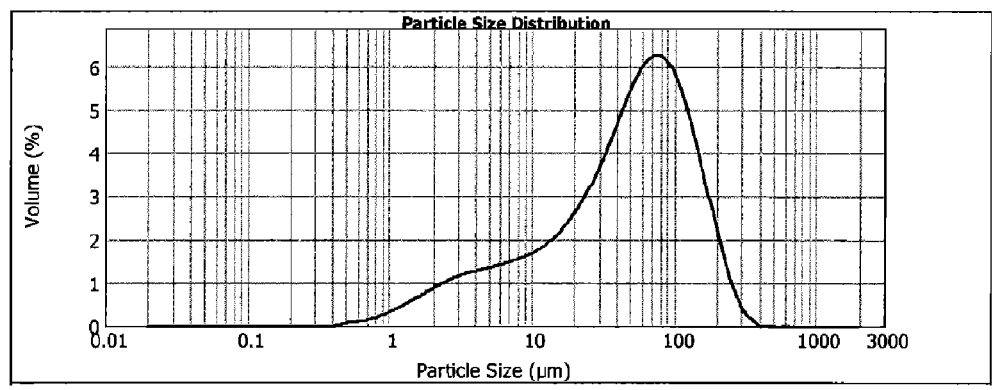
FIG. 5 shows a particle size distribution curve for the product of Example 6b.

Particle size distribution curves for Examples 6a and 6b are shown in FIGS. 4 and 5, respectively.

Abbreviations

Mol moles
g grams
mg milligrams
μg micrograms
eq. molar equivalents
mL milliliters
hr hours
EtOH ethanol
MeOH methanol
kPa kilopascals

The invention claimed is:

1. A process for the formation of hydrocodone bitartrate, which process comprises the steps:
   (i) providing a solution comprising hydrocodone and a first portion of tartaric acid;
   (ii) adjusting the temperature of the solution to less than about 50° C. and forming a precipitate comprising a tartaric acid salt of hydrocodone from said solution; and
   (iii) adding a second portion of tartaric acid to the product formed in step (ii),
   wherein the second portion of tartaric acid is added continuously over a period of at least 0.25 hr.

2. The process as claimed in claim 1, wherein the precipitate in step (ii) is formed as a free flowing slurry.

3. The process as claimed in claim 1, wherein the product of step (ii) comprises a tartaric acid salt of hydrocodone having a bulk density of from about 0.60 g/ml to about 0.70 g/ml.

4. The process of claim 1, wherein the product of step (ii) comprises a tartaric acid salt of hydrocodone in which at least 80% by volume of the particles of the tartaric acid salt of hydrocodone have a diameter that is from about 0.5 μm to about 2000 μm.

5. The process of claim 1, wherein in step (ii) the temperature of the solution of step (i) is adjusted to less than about 40° C.

6. The process of claim 1, wherein, in step (i), the solution is heated to a temperature of from about 40° C. to about 100° C.

7. The process of claim 1, wherein, in step (i), the first portion of tartaric acid comprises from about 0.2 to about 0.8 molar equivalents of tartaric acid with respect to the hydrocodone.

8. The process of claim 1, wherein the second portion of tartaric acid comprises from about 0.2 to about 0.8 molar equivalents of tartaric acid with respect to the hydrocodone.

9. The process of claim 1, wherein, in the product of step (i), greater than about 90% by weight of the hydrocodone is dissolved in the solution.

10. The process of claim 1, wherein, in the product of step (ii), from about 30% to about 90% by weight of the hydrocodone is present in solid form.

11. The process of claim 1, where the total amount of tartaric acid added in step (i) and step (iii) is from about 1.0 to about 1.2 molar equivalents with respect to the hydrocodone.

12. The process of claim 1, wherein said process further comprises the step of isolating the hydrocodone bitartrate from the product of step (iii).

13. The process of claim 12, wherein said process further comprises the steps of:
  (i) reslurrying the hydrocodone bitartrate obtained following the isolation step in a solvent or solvent mixture;
  (ii) isolating the solid hydrocodone bitartrate from that slurry; and
  (iii) optionally repeating steps (i) and (ii) one or more times.

14. A process for the formation of a pharmaceutical composition comprising hydrocodone bitartrate which process comprises the steps:
  (i) obtaining hydrocodone bitartrate according to a process of claim 1; and
  (iii) bringing the hydrocodone bitartrate into association with one or more pharmaceutically acceptable excipients, diluents or carriers.

15. The process of claim 1, wherein the product of step (ii) comprises a tartaric acid salt of hydrocodone in which at least 80% by volume of the particles of the tartaric acid salt of hydrocodone have a diameter that is from about 1 μm to about 1000 μm.

16. The process of claim 1, wherein in step (ii) the temperature of the solution of step (i) is adjusted to less than about 30° C.

17. The process of claim 1, wherein, in step (i), the first portion of tartaric acid comprises from about 0.4 to about 0.6 molar equivalents of tartaric acid with respect to the hydrocodone.

18. The process of claim 1, wherein the second portion of tartaric acid comprises from about 0.5 to about 0.6 molar equivalents of tartaric acid with respect to the hydrocodone.

* * * * *